United States Patent [19]

Arai et al.

[11] Patent Number: 5,149,852
[45] Date of Patent: Sep. 22, 1992

[54] PROCESS FOR CONCENTRATION AND SEPARATION OF HIGHLY UNSATURATED FATTY ACID ESTER

[75] Inventors: Makoto Arai; Hideki Fukuda, both of Takasago, Japan

[73] Assignee: Kanegafuchi Kagaku Kogyo Kabushiki Kaisha, Osaka, Japan

[21] Appl. No.: 676,470

[22] Filed: Mar. 27, 1991

Related U.S. Application Data

[63] Continuation of Ser. No. 196,529, May 20, 1988, abandoned.

[30] Foreign Application Priority Data

May 22, 1987 [JP] Japan .................. 62-125076

[51] Int. Cl.$^5$ .................. C07B 63/00; C07C 67/56; C07C 69/24; C07C 69/30
[52] U.S. Cl. .................. 554/193; 554/170; 554/172; 554/173; 554/191; 554/224
[58] Field of Search .................. 260/421, 428.5, 428, 260/410.9 R, 412, 412.5, 410.6, 410.7

[56] References Cited

U.S. PATENT DOCUMENTS

| 4,049,688 | 9/1977 | Neuzil et al. | 260/428 |
| 4,066,677 | 1/1978 | de Rosset et al. | 260/428.5 |
| 4,210,594 | 7/1980 | Logan et al. | 260/428.5 |
| 4,213,913 | 7/1980 | de Rosset et al. | 260/428.5 |

FOREIGN PATENT DOCUMENTS

| 0001854 | 5/1979 | European Pat. Off. . |
| 0002545 | 6/1979 | European Pat. Off. . |
| 0062113 | 10/1982 | European Pat. Off. . |
| 59-67245 | 4/1984 | Japan . |

*Primary Examiner*—Vivian Garner
*Attorney, Agent, or Firm*—Armstrong & Kubovcik

[57] ABSTRACT

This invention provides a process for concentration and separation of an eicosapentaenoic acid ester comprising:

(1) a step in which a solution, in a nonpolar solvent, of a mixture of fatty acid esters containing an eicosapentaenoic acid ester is allowed to contact with a zeolite, so as to allow said eicosapentaenoic ester to be adsorbed on said zeolite;

(2) a step in which said zeolite is allowed to contact with a nonpolar solvent, so as to desorb impurities; and (3) a step in which said zeolite is allowed to contact with a polar solvent, so as to allow said eicosapentaenoic acid ester to be desorbed.

This process makes it possible to obtain a highly pure eicosapentaenoic acid ester on a commercial scale.

7 Claims, No Drawings prising:

PROCESS FOR CONCENTRATION AND SEPARATION OF HIGHLY UNSATURATED FATTY ACID ESTER

This application is a continuation of application Ser. No. 196,529 filed May 20, 1988, abandoned.

BACKGROUND OF THE INVENTION

1. Filed of the Invention

The present invention relates to a process for concentration and separation of an eicosapentaenoic acid ester based on the difference in affinity of highly unsaturated fatty acid esters for zeolites.

2. Description of the Prior Art

Eicosapentaenoic acid (hereinafter abbreviated as EPA) is a kind of highly unsaturated (or polyunsaturated) fatty acid, which is commonly contained in fish oils, etc. EPA is an important substance as a precursor of prostaglandin and has been used as a nutritious additive for foods and the like. It was recently found that EPA was effective for various diseases, including blocking arteriosclerosis, and the like, and hence its demand as a medicine has been increasing quite rapidly.

In order to utilize EPA as a medicine, it must be separated from a mixture of fatty acids containing EPA up to a purity of at least 90%. Hitherto known processes for concentrating and separating unsaturated fatty acid esters, such as EPA ester, from their mixtures include a urea complex method (see British Patent No. 1240513) and a silver complex method (see the same patent), as well as an enzyme method, low temperature fractional crystallization methods, supercritical fluid extraction method, molecular distillation method, and the like. However, many problems arise with regard to purity, cost, operation, etc., when these methods are applied to concentration and separation of an EPA ester from a mixture of fatty acid esters containing the EPA ester, and therefore it is hardly possible to obtain highly pure EPA ester on an industrial scale. In Japanese Patent Application (Laid Open) No. 67,245/84 is disclosed a process for concentrating and separating an EPA ester and a docosahexaenoic acid ester, using a zeolite having a pore size of 5 to 13 Å. In this case, too, it is hardly possible to obtain the EPA ester having a purity of 90% or higher.

SUMMARY OF THE INVENTION

It is an object of the invention to provide a process for obtaining on a commercial scale an EPA ester having a purity of at least 90%, from a mixture of fatty acid esters containing said EPA ester.

Other objects and advantages of the invention will become apparent to those skilled in the art from the following description.

In order to achieve the above objects, the present inventors have conducted intensive studies and, as a result, have found that a highly pure EPA ester can be readily obtained through adsorption and desorption operations utilizing zeolites. The present invention has been accomplished on the basis of the above finding.

DETAILED DESCRIPTION OF THE INVENTION

There is provided by the present invention a process for concentration and separation of an EPA ester comprising:

(1) a step in which a solution in a nonpolar solvent of a mixture of fatty acid esters containing an EPA ester is allowed to contact with a zeolite so as to allow the EPA ester to be adsorbed on said zeolite;
(2) a step in which said zeolite is allowed to contact with a nonpolar solvent so as to desorb impurities; and
(3) a step in which said zeolite is allowed to contact with a polar solvent so as to desorb said EPA ester.

Fatty acid esters to be used in the process of the invention include esters obtained from oils and fats containing EPA and a lower alcohol, such as methanol, ethanol, propanol, butanol, and the like. It is also possible to use fatty acid esters of polyhydric alcohols, such as glycol and glycerol. As examples of oils and fats containing EPA, mention may be made of oils of such fish as sardines and mackerels; and animal and vegetable oils, such as liver oil, and the like. These oils and fats are converted to fatty acid esters through ester exchange in the presence of the above-described alcohols and a catalyst.

In the concentration and separation process of the invention, any zeolite containing the specified metallic cations can be used. However, it is preferable in respect of selectivity of adsorption to use zeolites containing alkyl ammonium cations. Such cation-containing zeolites can be obtained by subjecting commercially available zeolites (such as X-type or Y-type zeolites) to, e.g., ion exchange or by synthesizing zeolites from raw materials added with a salt of an alkylammonium ion. The ion exchange of zeolite may be carried out in accordance with well-known methods. For example, a zeolite is immersed in an aqueous solution of salts containing cations to be exchanged, for example, methyl ammonium ions, ethyl ammonium ions, n-propyl ammonium ions or i-propyl ammonium ions, and the immersed solution is stirred at a temperature of from 70° to 100° C. for about 24 hours. This treatment is repeated several times, and the thus treated zeolite is dried in the atmosphere at a temperature of 120° to 500° C.

Zeolites to be used in the process of the invention may be of any shape, including powders, pellets, beads, granules, and the like.

Examples of nonpolar solvents usable in the invention include both straight chain or cyclic nonpolar solvents, such as n-pentane, n-hexane, n-heptane, n-octane, cyclohexane and benzene. It is also possible to use a mixture of two or more of these solvents.

Examples of polar solvents usable in the desorption step of the invention include ketones, such as acetone, methyl ethyl ketone and diethyl ketone; lower alcohols, such as methanol, ethanol and butanol; halogenated hydrocarbons, such as chloroform and ethyl bromide; ethers, such as diethyl ether and isopropyl ether; acetates, such as ethyl acetate and methyl acetate; polar aromatic hydrocarbons, such as toluene and xylene; and the like. It is said that the molecules of these polar solvents have an electric dipole and hence exhibit a strong interaction with zeolites. This is presumably the reason why they are capable of desorbing fatty acid esters adsorbed on zeolites. It is possible to use a mixture of two or more polar solvents, or a mixture of one or more polar solvents and one or more nonpolar solvents. In respect of purity of EPA ester, it is particularly preferable to use a mixture of one or more nonpolar solvents and 0.01 to 10%, based on the volume of the nonpolar solvents, of one or more of those polar solvents described hereinabove.

The contact of zeolite with a mixture of fatty acid esters and solvents can be carried out in the conventional temperature range (from ca. 10° to ca. 90° C.) where adsorption operations are usually carried out. If the temperature is too low, impurities will be adsorbed in undesirably large quantities. On the other hand, if it is too high, the unsaturated fatty acids tend to be deteriorated. In addition, if the temperature is higher than the boiling point of the solvent(s) used, the operation must be carried out at a high pressure, which is disadvantageous from economical viewpoint. It can be particularly advantageous to carry out the operation at a temperature in the range of 20° to 50° C.

In the adsorption step in the process of the invention, fatty acid ester containing an EPA ester is dissolved in a nonpolar solvent and, (1) the resulting solution is charged into a vessel, added with a zeolite in an amount of 0.05 to 5 times the weight of said mixture of fatty acid esters and stirred for 0.5 to 10 hours so as to selectively adsorb the EPA ester, or (2) the solution is passed through a column filled with a zeolite so as to selectively adsorb the EPA ester. In the column operation (2) described above, the solution can be passed through the column at any rate if the EPA ester could be adsorbed by the zeolite. It is however preferable to pass the solution at a liquid hourly space velocity (LHSV) of 0.5 to 10. When the column operation is carried out at a pressure higher than atmospheric pressure, for example, at 10 to 100 kg/cm², a compact separation column may be used. The column operation is advantageous if an EPA ester having a particularly high purity is to be obtained.

Then, a nonpolar solvent is allowed to contact with the zeolite in order to desorb such impurities as esters of oleic acid, esters of linoleic acid, and the like.

In cases where the operation (1) is adopted, the nonpolar solvent in the vessel is filtered off, and a fresh nonpolar solvent is added thereto and then well stirred. This treatment is repeated one to ten times so as to desorb impurities. There is no particular limitation on the amount of the nonpolar solvent to be used. However, it is preferable to use a nonpolar solvent in an amount of 0.5 to 1,000 times the weight of the zeolite. In the case of the operation (2), impurities are desorbed by passing a nonpolar solvent through the column. During the desorption, the solvent can be passed at any rate if its quantity is enough to desorb the impurities. It is however preferable to pass the solvent at a liquid hourly space velocity of 0.5 to 10, as in the case of adsorption.

The EPA ester is then desorbed by allowing a polar solvent to contact with the zeolite. In cases where the operation (1) is adopted, the nonpolar solvent contained in the vessel is removed off by filtration, and a polar solvent is added thereto in an amount of 0.5 to 30 times the weight of the zeolite and then stirred for 0.5 to 5 hours. This treatment is repeated 1 to 5 times, so as to concentrate and separate the EPA ester. In cases where the operation (2) is adopted, the EPA ester may be desorbed by passing a polar solvent through the column filled with zeolite. The polar solvent can be passed through the column at any rate if the adsorbed EPA ester can be desorbed. However, it is particularly effective to pass a polar solvent at a liquid hourly space velocity of 0.05 to 10. In respect of purity of EPA ester, it may be advantageous to divide the eluate into 2 to 100 fractions, in the order of the affinity with zeolite. The EPA ester may be fractioned effectively by using two or more polar solvents, thereby passing a mixture of solvents with a gradually increasing polarity.

If a polar solvent is allowed to contact with the zeolite immediately after the adsorption step, it is impossible to obtain a highly pure EPA ester since impurities are desorbed at the same time in large quantities. For example, in the case where a n-propylammonium Y zeolite is used as an adsorbent and a polar solvent is allowed to contact with the zeolite immediately after the adsorption step, there will only be obtained an EPA ester having a purity of at most 90%. However, when the zeolite, after the adsorption step, is once allowed to contact with a nonpolar solvent and then with a polar solvent, an EPA ester having a purity of ca. 98% can be readily obtained.

The solvent in the fractions containing the EPA ester at a high concentration is removed off by means of distillation, thereby giving an EPA ester having a purity of 90% or above. Fatty acid esters contained in other fractions can also be recovered in the same manner. The zeolite can be used repeatedly by, after the completion of the fractionation, being washed with a nonpolar solvent or being dried at a temperature of 100° to 500° C.

As described hereinabove, the process of the present invention is quite simple in its operation, compared with the prior processes employed for the concentration and separation of EPA esters. In addition, the process is advantageous in cost and, therefore, highly promising in industrial application.

The invention will further be illustrated by way of examples. It would however be understood that the invention is by no means limited to them. In the following examples, all the precentages (%) are based on weight unless otherwise specified.

EXAMPLE 1

Into flasks were placed 5 g of sodium Y zeolite (trade name "TSZ-320 NAD", manufactured by Toyo Soda Manufacturing Co., Ltd.) or sodium X zeolite (trade name "Molecular Sieves 13X", manufactured by Union Carbide Corp.) and 100 ml of 1N aqueous solutions of each of various salts, and the contents of the flasks were stirred at ca. 80° C. for 24 hours so as to exchange the sodium ion with a variety of ions, washed with water and then dried at 160° C. for 1 hour.

On the other hand, a fish oil obtained from sardine, mackerel, or the like was subjected to ester exchange, using 0.2N NaOH solution in ethanol to obtain a mixture of esters of fatty acids having the composition shown in Table 1. In the table, $C_{n:k}$ indicates a fatty acid ester defined by the molecular formula: $C_{n-1}H_{2(n-k)-1}COOC_2H_5$.

To 10 g of the mixture of the fatty acid esters was added 100 ml of n-hexane, and the solution obtained was passed through a glass column having an inner diameter of 1.0 cm and a length of 10 cm, filled with 5.0 g of various zeolites prepared above. Thereafter, 250 ml of n-hexane was passed through the column and then 250 ml of n-hexane mixed with 0.5% by volume of ethanol. During this operation, the column was maintained at 30° C. under atmospheric pressure. The elution was carried out at a liquid hourly space velocity of 1.0 [1./hr.], and the eluate was divided into 25 ml fractions.

The solvents of fractions Nos. 16 to 19 were distilled off. The total amount of fatty acid esters obtained and their compositions are shown in Table 2.

The above procedure was repeated by using the same sodium Y zeolite and sodium X zeolite without subjecting them to the ion exchange treatment. Results obtained are also shown in Table 2.

TABLE 1

| Component | C 14:0 | C 16:0 | C 16:1 | C 18:0 | C 18:1 | C 18:2 | C 20:5 (EPA) | C 22:6 | Others |
|---|---|---|---|---|---|---|---|---|---|
| Composition (%) | 8.1 | 17.7 | 7.7 | 2.2 | 11.9 | 2.1 | 12.9 | 9.8 | 27.6 |

TABLE 2

| Absorbent | Amount of Oil (g) | C 14:0 | C 16:0 | C 16:1 | C 18:0 | C 18:1 | C 18:2 | C 20:5 (EPA) | C 22:6 | Others (%) |
|---|---|---|---|---|---|---|---|---|---|---|
| Sodium Y | 0.486 | 3.9 | 6.3 | 2.7 | 0.1 | 3.9 | 2.4 | 34.8 | 28.4 | 17.5 |
| Cesium Y | 0.498 | 0.1 | 0.1 | 0.1 | 0.1 | 0.1 | 0.2 | 89.1 | 5.2 | 5.0 |
| Methyl Ammonium Y | 0.201 | 0.0 | 0.0 | 0.1 | 0.0 | 0.1 | 0.1 | 97.8 | 0.2 | 1.7 |
| Ethyl Ammonium Y | 0.285 | 0.0 | 0.0 | 0.1 | 0.0 | 0.1 | 0.2 | 97.3 | 1.1 | 1.2 |
| n-Propyl Ammonium Y | 0.238 | 0.0 | 0.0 | 0.0 | 0.0 | 0.1 | 0.1 | 98.5 | 0.3 | 1.0 |
| n-Butyl Ammonium Y | 0.219 | 0.0 | 0.0 | 0.0 | 0.0 | 0.0 | 0.2 | 98.7 | 0.3 | 0.8 |
| Sodium X | 0.338 | 4.6 | 9.5 | 4.4 | 0.6 | 5.6 | 1.8 | 30.1 | 24.8 | 18.6 |
| Methyl Ammonium X | 0.251 | 0.0 | 0.0 | 0.1 | 0.0 | 0.1 | 0.2 | 97.2 | 0.2 | 2.2 |
| n-Propyl Ammonium X | 0.188 | 0.1 | 0.0 | 0.1 | 0.0 | 0.3 | 0.2 | 98.0 | 0.9 | 0.4 |

It would be understood from the Table 2 that the use of a zeolite containing an alkylammonium cation makes it possible to markedly improve the purity of the EPA ester.

On the other hand, in cases where 250 ml of n-hexane mixed with 0.5% by volume of ethanol was passed through a column immediately after the adsorption of the fatty acid esters, there were obtained EPA esters having a purity not higher than 90%.

What is claimed is:

1. A process for the separation of an eicosapentaenoic acid ester having a purity of at least 90% from a mixture of fatty acid esters containing the eicosapentaenoic acid ester, which comprises:

contacting the mixture dissolved in hexane with a zeolite containing alkylammonium cations having 1 to 4 carbon atoms to absorb the eicosapentaenoic acid ester;

washing the zeolite with hexane to desorb impurities; and washing the zeolite with hexane mixed with 0.01 to 10% of ethanol, based on the volume of the nonpolar solvent, to desorb eicosapentaenoic acid ester having a purity of at least 90%.

2. A process as defined in claim 1, wherein a mixture of fatty acid esters containing an eicosapentaenoic acid ester is dissolved in hexane, the resulting solution was added with a zeolite in an amount of 0.05 to 5 times the volume of said mixture of fatty acid esters and then stirred for 0.5 to 10 hours, so as to selectively absorb said eicosapentaenoic acid ester by a batch method.

3. A process as defined in claim 1, wherein the hexane is added in an amount of 0.5 to 1,000 times the weight of said zeolite, so as to desorb impurities by a batch method.

4. A process as defined in claim 1, wherein the ethanol is added in an amount of 0.5 to 30 times the weight of said zeolite, the resulting mixture is stirred for 0.5 to 5 hours, and this treatment is repeated one to five times, so as to desorb said eicosapentaenoic acid ester by a batch method.

5. A process as defined in claim 1, wherein the solution of a mixture of fatty acid esters containing an eicosapentaenoic acid ester is passed through a column filled with a zeolite at a liquid hourly space velocity of 0.5 to 10, so as to allow said eicosapentaenoic acid ester to be selectively adsorbed.

6. A process as defined in claim 1, wherein the hexane is passed through a column at a liquid hourly space velocity of 0.5 to 10, so as to desorb impurities.

7. A process as defined in claim 1, wherein the ethanol is passed through a column at a liquid hourly space velocity of 0.05 to 10, so as to desorb said eicosapentaenoic acid ester.

* * * * *